(12) United States Patent
Bhattacharya

(10) Patent No.: US 12,605,078 B2
(45) Date of Patent: *Apr. 21, 2026

(54) METHOD AND APPARATUS FOR CONTINUOUS VITALS MONITORING

(71) Applicant: Rythmos LLC, Edina, MN (US)

(72) Inventor: Manojeet Bhattacharya, Edina, MN (US)

(73) Assignee: Rythmos LLC, Edina, MN (US)

( * ) Notice: Subject to any disclaimer, the term of this patent is extended or adjusted under 35 U.S.C. 154(b) by 627 days.

This patent is subject to a terminal disclaimer.

(21) Appl. No.: 18/050,756

(22) Filed: Oct. 28, 2022

(65) Prior Publication Data

US 2023/0070912 A1      Mar. 9, 2023

Related U.S. Application Data

(63) Continuation-in-part of application No. 16/723,078, filed on Dec. 20, 2019, now Pat. No. 11,504,010.

(51) Int. Cl.
A61B 5/0205 (2006.01)
A61B 5/00 (2006.01)
(Continued)

(52) U.S. Cl.
CPC ...... A61B 5/02055 (2013.01); A61B 5/14532 (2013.01); A61B 5/14552 (2013.01);
(Continued)

(58) Field of Classification Search
CPC ............ A61B 5/02055; A61B 5/14532; A61B 5/14552; A61B 5/681; A61B 5/7425;
(Continued)

(56) References Cited

U.S. PATENT DOCUMENTS

| | | | |
|---|---|---|---|
| 4,868,381 A | 9/1989 | Davis | |
| 4,909,260 A | 3/1990 | Salem et al. | |

(Continued)

FOREIGN PATENT DOCUMENTS

| | | |
|---|---|---|
| CN | 103596494 A | 2/2014 |
| CN | 103607949 A | 2/2014 |

(Continued)

OTHER PUBLICATIONS

Anzai Medical, Co., Ltd, "Respiratory Gating System AZ-733V1: What is a Respiratory Gating System," [retrieved online Jan. 10, 2024] http://www.anzai-med.co.jp, publication date unknown, 4 pages.

(Continued)

*Primary Examiner* — Brian T Gedeon
(74) *Attorney, Agent, or Firm* — TraskBritt

(57) ABSTRACT

A health monitoring device for detecting a physiological attribute having a physiological attribute sensor including a first fiber Bragg grating (FBG) with a refractive index is configured to be placed in contact with a person's skin approximate to an artery or vein. A baseline sensor that includes a second fiber Bragg grating (FBG) also having a refractive index is configured to be placed in contact with a person's skin away from an artery or vein to provide a baseline refractive index. The device pulses light waves through the FBGs to provide a processor with reading of the refractive index from the FBGs. Based on the effective shifts of the Bragg wavelength due to axial strain on the FBGs, a physiological attribute estimator estimates a physiological attribute based on a calibration curve comparing a physiological attribute against strain.

20 Claims, 7 Drawing Sheets

(51) Int. Cl.

| | |
|---|---|
| *A61B 5/021* | (2006.01) |
| *A61B 5/024* | (2006.01) |
| *A61B 5/145* | (2006.01) |
| *A61B 5/1455* | (2006.01) |

(52) U.S. Cl.
CPC ............ *A61B 5/681* (2013.01); *A61B 5/7425* (2013.01); *A61B 5/021* (2013.01); *A61B 5/02427* (2013.01); *A61B 2560/0223* (2013.01); *A61B 2562/0233* (2013.01)

(58) Field of Classification Search
CPC ... A61B 5/021; A61B 5/02427; A61B 5/0002; A61B 5/01; A61B 5/1455; A61B 2560/0223; A61B 2560/0233
See application file for complete search history.

(56) References Cited

U.S. PATENT DOCUMENTS

| | | | |
|---|---|---|---|
| 5,545,993 | A | 8/1996 | Taguchi et al. |
| 5,907,403 | A | 5/1999 | Andrews et al. |
| 6,475,153 | B1 | 11/2002 | Khair et al. |
| 7,077,810 | B2 | 7/2006 | Lange et al. |
| 7,257,436 | B2 | 8/2007 | Sasaki et al. |
| 7,678,063 | B2 | 3/2010 | Felmlee et al. |
| 8,553,959 | B2 | 10/2013 | Hsieh et al. |
| 8,655,441 | B2 | 2/2014 | Fletcher et al. |
| 9,088,130 | B2 | 7/2015 | Kim et al. |
| 9,116,055 | B2 | 8/2015 | Johnston |
| 9,304,018 | B2 | 4/2016 | Davis et al. |
| 9,730,654 | B2 | 8/2017 | Erbel et al. |
| 9,841,331 | B2 | 12/2017 | Wood et al. |
| 9,987,503 | B2 | 6/2018 | Grass et al. |
| 10,234,934 | B2 | 3/2019 | Connor |
| 10,321,873 | B2 | 6/2019 | Connor |
| 10,332,644 | B2 | 6/2019 | Garcia |
| 10,488,916 | B2 | 11/2019 | Hahami et al. |
| 10,524,701 | B2 | 1/2020 | Kim et al. |
| 10,716,510 | B2 | 7/2020 | Connor |
| 11,041,740 | B1 | 6/2021 | Bhattacharya |
| 11,504,010 | B2 | 11/2022 | Bhattacharya |
| 12,044,556 | B2 | 7/2024 | Bhattacharya |
| 12,209,891 | B2 | 1/2025 | Bhattacharya |
| 12,209,892 | B1 | 1/2025 | Bhattacharya |
| 2005/0192508 | A1 | 9/2005 | Lange et al. |
| 2008/0045813 | A1 | 2/2008 | Phuah et al. |
| 2008/0146947 | A1 | 6/2008 | Kojima et al. |
| 2008/0300502 | A1 | 12/2008 | Yang et al. |
| 2009/0185772 | A1 | 7/2009 | Xia et al. |
| 2009/0234240 | A1 | 9/2009 | Kuenzler et al. |
| 2013/0035587 | A1 | 2/2013 | Lagendijk et al. |
| 2013/0211261 | A1 | 8/2013 | Wang et al. |
| 2014/0064332 | A1 | 3/2014 | Johnston |
| 2014/0088377 | A1 | 3/2014 | Manske et al. |
| 2014/0128721 | A1 | 5/2014 | Forthmann et al. |
| 2014/0193058 | A1 | 7/2014 | Bharat et al. |
| 2014/0194703 | A1 | 7/2014 | Wondka et al. |
| 2014/0238153 | A1 | 8/2014 | Wood et al. |
| 2014/0268099 | A1 | 9/2014 | Moslehi |
| 2015/0018596 | A1 | 1/2015 | Schulz et al. |
| 2015/0119703 | A1 | 4/2015 | Mitchell et al. |
| 2015/0124266 | A1 | 5/2015 | Davis et al. |
| 2015/0289785 | A1 | 10/2015 | Bojovic et al. |
| 2015/0359455 | A1 | 12/2015 | Hahami et al. |
| 2015/0359467 | A1 | 12/2015 | Tran |
| 2016/0202755 | A1 | 7/2016 | Connor |
| 2016/0256710 | A1 | 9/2016 | Goldstein et al. |
| 2016/0338644 | A1 | 11/2016 | Connor |
| 2016/0361194 | A1 | 12/2016 | Hautvast et al. |
| 2017/0007849 | A1 | 1/2017 | Hautvast et al. |
| 2017/0049341 | A1 | 2/2017 | Karabacak et al. |
| 2017/0354353 | A1 | 12/2017 | Kim et al. |
| 2018/0008196 | A1 | 1/2018 | Connor |
| 2018/0364115 | A1 | 12/2018 | Brown et al. |

| | | | |
|---|---|---|---|
| 2019/0223782 | A1 | 7/2019 | Wen et al. |
| 2019/0298265 | A1 | 10/2019 | Keating et al. |
| 2019/0336038 | A1 | 11/2019 | Gorgutsa et al. |
| 2021/0186340 | A1 | 6/2021 | Bhattacharya |
| 2021/0190549 | A1 | 6/2021 | Bhattacharya |
| 2021/0223068 | A1 | 7/2021 | Bhattacharya |
| 2024/0032816 | A1 | 2/2024 | Bhattacharya |
| 2024/0210218 | A1 | 6/2024 | Bhattacharya |
| 2025/0003774 | A1 | 1/2025 | Bhattacharya |
| 2025/0020491 | A1 | 1/2025 | Bhattacharya |
| 2025/0172414 | A1 | 5/2025 | Bhattacharya |
| 2025/0172415 | A1 | 5/2025 | Bhattacharya |

FOREIGN PATENT DOCUMENTS

| | | | |
|---|---|---|---|
| CN | 103889259 | A | 6/2014 |
| CN | 103889506 | A | 6/2014 |
| CN | 106029172 | A | 10/2016 |
| CN | 110192854 | A | 9/2019 |
| CN | 110301906 | A | 10/2019 |
| CN | 209574670 | U | 11/2019 |
| CN | 111317481 | A | 6/2020 |
| JP | H0775627 | A | 3/1995 |
| JP | 2002175582 | A | 6/2002 |
| JP | 2007185300 | A | 7/2007 |
| JP | 2007525267 | A | 9/2007 |
| JP | 2007537777 | A | 12/2007 |
| JP | 2009501557 | A | 1/2009 |
| JP | 2011509764 | A | 3/2011 |
| JP | 2014525764 | A | 10/2014 |
| JP | 2015231512 | A | 12/2015 |
| JP | 2017506543 | A | 3/2017 |
| JP | 2017506555 | A | 3/2017 |
| JP | 2017519221 | A | 7/2017 |
| WO | WO-02069878 | A2 | 9/2002 |
| WO | WO-2012168836 | A2 | 12/2012 |
| WO | 2013/180085 | A1 | 12/2013 |
| WO | WO-2015128179 | A1 | 9/2015 |
| WO | WO-2015128392 | A1 | 9/2015 |
| WO | 2015/167340 | A1 | 11/2015 |
| WO | WO-2016070099 | A1 | 5/2016 |
| WO | WO-2016147795 | A1 | 9/2016 |
| WO | 2017/037479 | A1 | 3/2017 |
| WO | WO-2017190085 | A1 | 11/2017 |
| WO | WO-2019031041 | A1 | 2/2019 |
| WO | WO-2020049291 | A1 | 3/2020 |
| WO | WO-2021127207 | A1 | 6/2021 |
| WO | WO-2021127233 | A1 | 6/2021 |
| WO | WO-2022020519 | A1 | 1/2022 |
| ZA | 200 508 066 | B | 1/2007 |

OTHER PUBLICATIONS

De Jonckheere, J., et al.; "OFSETH: A breathing motions monitoring system for patients under MRI," 32nd Annual International Conference of the IEEE EMBS, 2010, pp. 1016-1019.

Extended European Search Report for European Application No. 21845416.3, mailed Jun. 14, 2024, 8 pages.

International Preliminary Report on Patentability for PCT/US2021/042641, mailed Jan. 24, 2023, 13 pages.

International Search Report and Written Opinion for PCT/US2021/042641, mailed Nov. 12, 2021, 14 pages.

Lau, Doreen, et al. "Intensity-Modulated Microbend Fiber Optic Sensor for Respiratory Monitoring and Gating During MRI," IEEE Transactions on Biomedical Engineering, vol. 60, No. 9, Sep. 2013, pp. 2655-2662.

Lui, J. et al, "Evaluation of the combined use of two different respiratory monitoring systems for 4D CT simulation and gated treatment," Journal of Applied Clinical Medical Physics, Wiley 19:5 pp. 666-675, (2018).

Non-Final Office Action for U.S. Appl. No. 16/723,078 dated Mar. 3, 2022, 13 pages.

Office Action for Japanese Application No. 2022-538268, mailed Oct. 29, 2024, with English translation, 7 pages.

Davies, J. et al, "Beyond blood pressure: pulse wave analysis—a better way of assessing cardiovascular risk?" Future Cardiology, 1(1):69-78 (2005).

(56)     References Cited

OTHER PUBLICATIONS

Esper, S. A., et al, "Arterial waveform analysis," Best Practice & Research Clinical Anaesthesiology, 28:363-380 (2014).

Khan, Y., et al, "A Flexible Organic Reflectance Oximeter Array," Proceedings of the National Academy of Sciences, 115(47):E11015-E11024 (Nov. 2018).

Lee, H. et al, "Reflectance pulse oximetry: Practical issues and limitation," The Korean Institute of Communications and Information Services, ScienceDirect; 195-198 (Nov. 2016).

Nekic, P., "Pulse Contour Cardiac Output (PiCCO) Learning Package," Liverpool Hospital Intensive Care Unit, pp. 1-17; (Feb. 29, 2016).

Roylance, D., "Stress-Strain Curves," Department of Materials Science and Engineering, Massachusetts Institute of Technology, Cambridge, MA, pp. 1-15, (Aug. 23, 2001).

International Search Report and Written Opinion for Int'l Application No. PCT/US2020/065652, titled: Wearable Health Monitoring Device, Date Mailed: Mar. 10, 2021.

Katsuragawa, Y. and Ishizawa, H., "Non-invasive Blood Pressure Measurement by Pulse Wave Analysis Using FBG Sensor," 2015 IEEE International Instrumentation and Measurement Technology Conference (12MTC) Proceedings, IEEE, pp. 511-515 (May 11, 2015).

Office Action for Chinese Application No. 202080087960.X, with English translation, dated Mar. 28, 2025, 11 pages.

Office Action for Chinese Application No. 202180049514.4, with English translation, dated Mar. 14, 2025, 21 pages.

Office Action for Japanese Application No. 2023-504460, dated Mar. 24, 2025, mailed May 27, 2025, with Search Report and English translation, 41 pages.

CN Application No. 202180049514.4, Office Action and Search Report mailed Oct. 29, 2025; Applicant Rythmos LLC, with English translation; 20 pages.

EP Application No. 25167563.3, Extended European Search Report mailed Oct. 22, 2025; Applicant Rythmos LLC; 11 pages.

U.S. Appl. No. 18/006,144, Non-Final Office Action mailed Aug. 22, 2025; Inventor Bhattacharya, Manojeet et al.; 28 pages.

INITIAL BLOOD PRESSURE TEST
510

ACQUIRE PEAK WAVELENGTH DATA FROM FBG PROXIMATE TO ARTERY AND TO BASELINE FBG
520

DETECT EFFECTIVE SHIFTS IN BRAGG WAVELENGTHS AND COMPARE BASELINE FBG WITH FBG PROXIMATE TO ARTERY
530

ESTIMATE BLOOD PRESSURE BASED ON CALIBRATION CURVE OF PRESSURE AGAINST STRAIN
540

DISPLAY BLOOD PRESSURE
550

METHOD AND APPARATUS FOR CONTINUOUS VITALS MONITORING

RELATED APPLICATION

This application is a continuation-in-part of U.S. application Ser. No. 16/723,078 (now U.S. Pat. No. 11,504,010), filed Dec. 20, 2019. The entire teachings of the above application are incorporated herein by reference.

BACKGROUND

A person's state of health is often measured against certain vital signs, including blood pressure, respiratory rate, heart rate, blood oxygen saturation, and body temperature. Blood pressure refers to the pressure of circulating blood on the walls of blood vessels as the heart pumps blood through the circulatory system. Blood pressure is typically expressed in terms of the systolic pressure (maximum during one heartbeat) over diastolic pressure (minimum between two heartbeats) and is measured in millimeters of mercury (mmHg), above the surrounding atmospheric pressure.

The normal resting blood pressure of an average an adult is approximately 120 mmHG systolic, and 80 mmHG diastolic (120/80). Blood pressure that is consistently high is referred to as hypertension, and low blood pressure is referred to as hypotension. Long-term hypertension is a risk factor for many diseases, including heart disease, stroke and kidney failure.

Blood pressure is commonly measured using a sphygmomanometer, which typically consists of an inflatable cuff, a measuring unit (e.g. a mercury manometer, or aneroid gauge), and a mechanism for inflation which may be a manually operated bulb and valve or a pump operated electrically. The inflatable cuff is placed around an upper arm (or in some cases, the wrist), and inflated to constrict the arm and the blood vessels within. By listening through a stethoscope at the brachial artery at the elbow, the examiner slowly releases the pressure in the cuff. As the pressure in the cuffs falls, a "whooshing" or pounding sound is heard when blood flow first starts again in the artery. The pressure at which this sound began is noted and recorded as the systolic blood pressure. The cuff pressure is further released until the sound can no longer be heard. This is recorded as the diastolic blood pressure. Digital instruments use a cuff which may be placed, according to the instrument, around the upper arm, wrist, or a finger, in all cases elevated to the same height as the heart. The automated instruments inflate the cuff and gradually reduce the pressure in the same way as a manual meter, and measure blood pressure using oscillometric methods that measure the oscillations in the cuff pressure induced by the blood pressure pulses.

More recently, methods and systems to measure blood pressure have been developed without applying any pressure (or by applying very minimal pressure) on patient's body. One method estimates blood pressure from the time difference (propagation velocity) between pulse waves measured by fiber Bragg grating sensors (herein "FBG sensors") attached to multiple locations on the subject.

SUMMARY

Embodiments of the present invention provide a wearable health monitoring device for detecting blood pressure. In one embodiment consistent with principles of the invention, a first fiber Bragg grating (FBG) is configured to be placed in contact with a person's skin approximate to an artery or vein. A second fiber Bragg grating (FBG) is configured to be placed in contact with a person's skin away from an artery or vein to provide a baseline. The device has a light emitter that pulses light waves through the FBGs, and light sensors that receive pulsed light waves to provide a processor with readings of effective Bragg wavelength ($\lambda_{eff}$) of the FBGs. It is known that $\lambda_{eff}$ of a FBG is a function of the temperature and the purpose of the second FBG is to measure the baseline that could change due to temperature changes or any other reason and then use it to correct the time varying $\lambda_{eff}$ shifts due to the blood pressure pulses in the first FBG that is in contact with the artery. A data acquisition module receives the light sensor peak wavelengths reflected by the FBGs. A comparator determines the effective shift of the Bragg wavelength due to axial strain on the FBGs resulting a complete measurement of the blood pressure pulse. A blood pressure estimator is configured to compute the entire blood pressure pulse and estimate systolic and diastolic blood pressures based on a calibration curve comparing pressure against strain, along effective shifts in the Bragg wavelength of the first FBG and the second FBG. The device uses a display to provide the blood pressure pulses and the estimated systolic and diastolic blood pressures.

Another embodiment consistent with principles of the invention include a heart rate monitor configured to detect periodic changes in surface deformation associated with a heartbeat, i.e., by counting the number of blood pressure pulses per unit of time as well as the time interval between blood pressure pulses for estimating the heart rate variability.

In addition to using FBGs to monitor blood pressure, some embodiments of a wearable heath monitor may also include a variety of physiological attribute or wellness monitors such as a blood oxygen saturation sensor that is either an integral part of the device or is an additional device in the form of a finger ring that is in communication with the health monitor via near field wireless communication, a blood glucose sensor that may be integral part of the device or a standalone device in wireless communication with the health monitoring device, an ECG monitor may be integral part of the device or a stand-alone device in wireless communication with the health monitoring device, and contact temperature sensor that measures the skin or body temperature sensor. For example, optical sensors or skin temperature sensors may be included in the device.

Embodiments of the device may also include a transmitter where the transmitter provides the blood pressure pulses and the estimated systolic and diastolic blood pressure information for display on a remote device. Such information could also be transmitted to the remote device for monitoring purposes and for data analysis for deriving health metrics.

Yet another embodiment of the present invention may include a plurality of fiber Bragg gratings (FBG) configured to be placed in contact with a person's skin close proximity to an artery or vein. Each FBG is displaced from one another by a predetermined amount.

Further embodiments include a health monitoring device. A blood pressure sensor including a first fiber Bragg grating (FBG) may be configured to be placed in contact with a person's skin approximate to an artery or vein and having a first Bragg wavelength. A baseline sensor including a second fiber Bragg grating (FBG) may be configured to be placed in contact with a person's skin away from the artery or vein and having a second Bragg wavelength and providing a measure of a baseline signal. A light emitter may be configured to pulse light waves through the FBGs. Light sensors may be configured to receive pulsed light waves. A processor may include 1) a data acquisition module configured to receive from the light sensor peak wavelengths reflected by the FBGs; 2) a comparator configured to determine effective shifts of the first Bragg wavelength and effective shifts of the second Bragg wavelength over time; and 3) a blood pressure estimator configured to estimate systolic and diastolic blood pressure based on 1) the effective shifts of the first Bragg wavelength corrected for drifts in the baseline signal based on the effective shifts of the second Bragg wavelength, and 2) an output of a physiological attribute monitor. A display may provide the estimated systolic and diastolic blood pressure.

The blood pressure estimator may be configured to estimate the systolic and diastolic blood pressure based on pulse transit times (PTT) between blood pressure pulses from the blood pressure sensor and the output, the output being one of an electrocardiogram (ECG) and a heart rate monitor. The processor may be further configured to determine a pulse pressure waveform based on the effective shifts of the first Bragg wavelength corrected for drifts in the baseline signal based on the effective shifts of the second Bragg wavelengths.

The processor may be further configured to analyze pulse pressure waveform features including at least one of a stroke volume and a dicrotic notch. A processor may be configured to analyze the blood pressure waveform to determine a cardiovascular parameter including at least one of stroke volume and cardiac output. A processor may be configured to perform a pattern recognition analysis of the blood pressure waveform to estimate a likelihood of a disease exhibited by the person. A processor may be configured to monitor changes to the blood pressure waveform to determine a likelihood of a cardiovascular disease.

The device may be implemented in a wearable band at the person's arm or wrist, the first and second FBGs being embedded within a strap of the wearable band. The physiological attribute monitor may be enclosed within the device the physiological attribute monitor including at least one of an ECG, a heartrate monitor, an oxygen saturation (SPO2) monitor, a blood glucose monitor, and a skin temperature monitor.

The blood pressure estimator may be configured to estimate the systolic and diastolic blood pressure based on a calibration function is derived from a timing correlation between the blood pressure sensor and an output of the physiological attribute monitor, the output being at least one of an ECG, heart rate, blood oxygen saturation. The processor may further include a heart rate monitor configured to detect periodic changes in surface deformation associated with a heartbeat. The physiological attribute monitor may measure one of an ECG, blood oxygen saturation, body temperature, and blood glucose measurements. The display may be located on a remote device, and the device may further include a transmitter configured to transmit estimated systolic and diastolic blood pressure to the display. The blood pressure sensor may further include a plurality of FBGs configured to be placed in contact with a person's skin close approximate to an artery or vein and having Bragg wavelengths, wherein each FBG is displaced from one another by a predetermined amount, and wherein the processor is configured to reconcile acquired data from the plurality of FBGs to optimize a measurement in effective shifts in Bragg wavelength of the blood pressure sensor.

Further embodiments include a method of monitoring health. Light waves may be pulsed through a first and second fiber Bragg gratings (FBGs) at 1) a blood pressure sensor including a first fiber Bragg grating (FBG) configured to be placed in contact with a person's skin approximate to an artery or vein and having a first Bragg wavelength, and 2) a baseline sensor including a second fiber Bragg grating (FBG) configured to be placed in contact with a person's skin away from the artery or vein and having a second Bragg wavelength and providing a measure of a baseline signal. Peak wavelengths reflected by the first and second FBGs may be obtained from a light sensor configured to receive pulsed light waves. Effective shifts of the first Bragg wavelength and effective shifts of the second Bragg wavelength over time may then be determined. Systolic and diastolic blood pressure may be estimated based on 1) the effective shifts of the first Bragg wavelength corrected for drifts in the baseline signal based on the effective shifts of the second Bragg wavelength, and 2) an output of a physiological attribute monitor. The estimated systolic and diastolic blood pressure may then be presented at a display.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Figure 1:
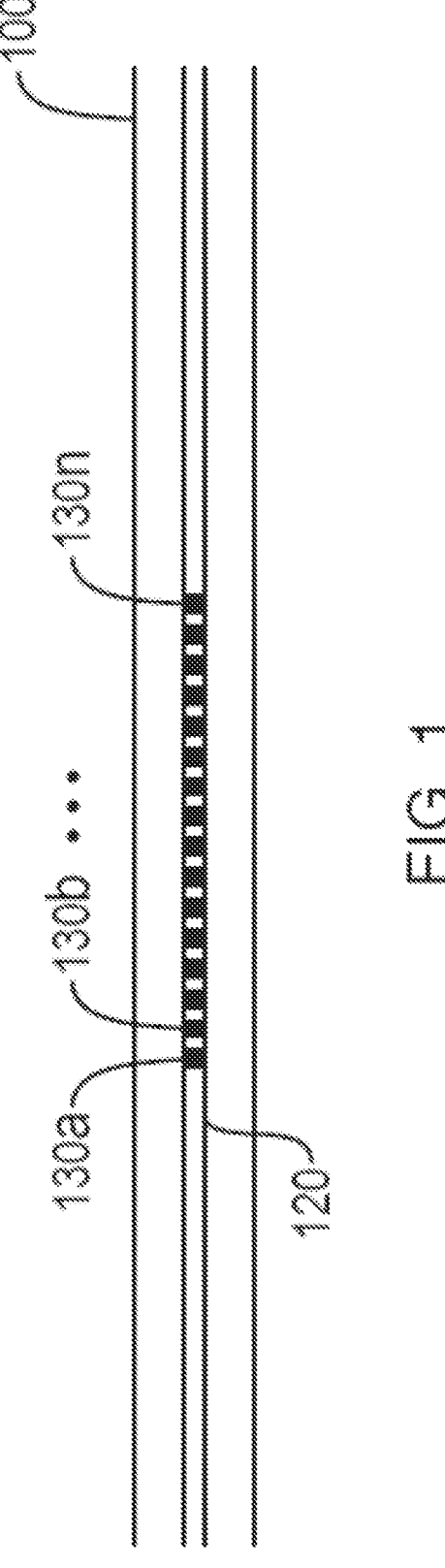
FIG. 1 is a representative FBG in a fiber-core.

As illustrated in FIG. 1, a Fiber Bragg grating (FBG) 100 is a small length of optical fiber 120 that comprises a plurality of reflection points 130$a$-$n$ that create a periodic variation of refractive index. The FBG reflects a unique wavelength ($\lambda$B), centered around a bandwidth, $\Delta\lambda$B. The periodicity $\Lambda$ of the grating is related to the Bragg wavelength $\lambda$B.

$$\lambda B = 2 \cdot \eta_{eff} \cdot \Lambda \tag{1}$$

$n_{eff}$ is the effective refractive index of the single-mode photosensitive fiber. As the fiber is stretched and grating parameter $\Lambda$ increases by $\delta\Lambda$ while effective refractive index $n_{eff}$ decreases by $\delta n_{eff}$. The Bragg wavelength $\lambda$B shifts by $$\delta\lambda B = 2\{n_{eff} \cdot \delta\Lambda + \Lambda \cdot \delta n_{eff}\} \tag{1a}$$

Figure 2:
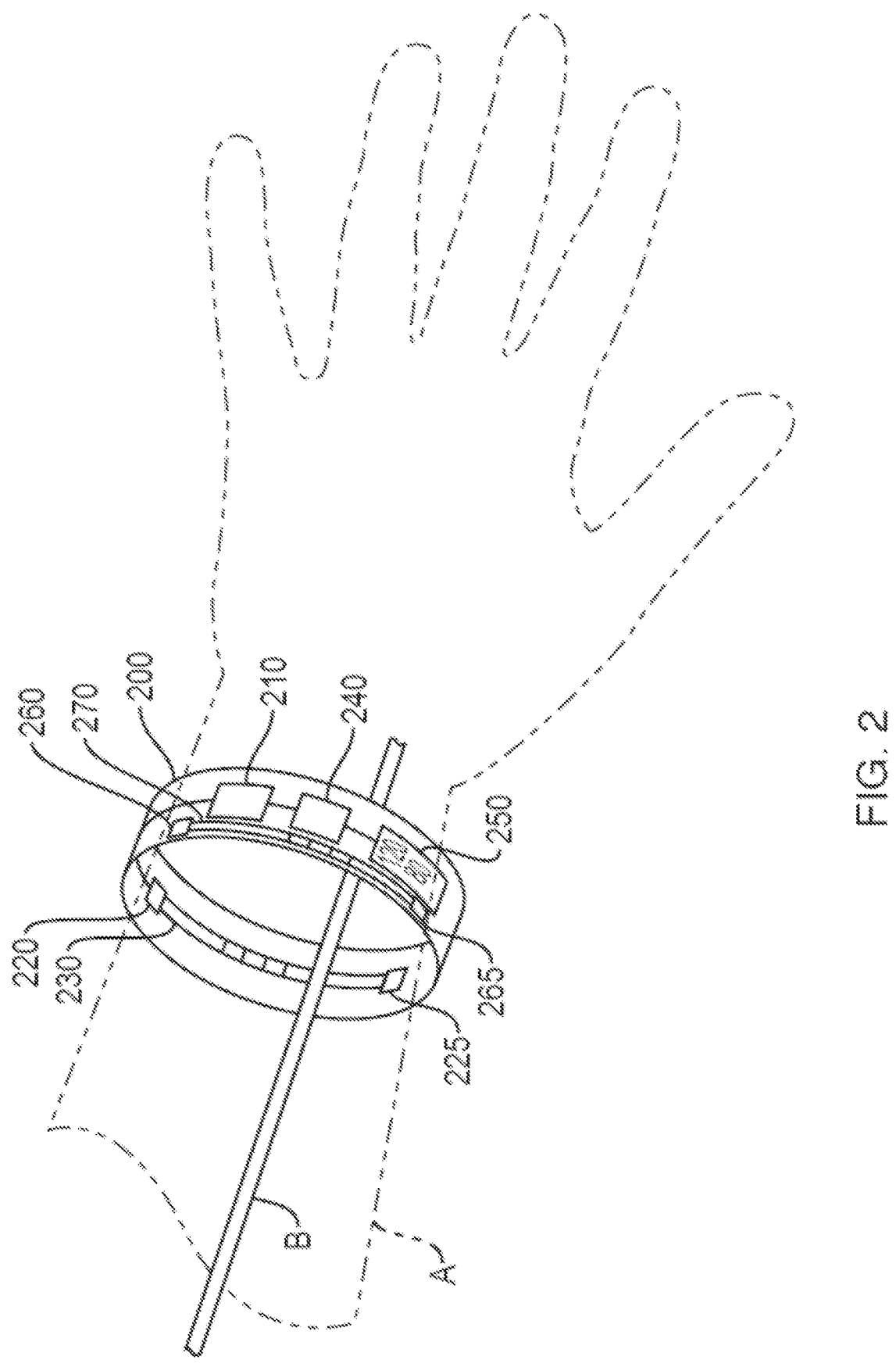
FIG. 2 is an exemplary wearable health monitoring device consistent with principles of the invention.

By embedding one or more optical fibers with one or more FBG in wearable materials that can be wrapped over parts of anatomically relevant parts of the human body, the wearable materials may be used to sense the surface deformation of that part resulting from physiological processes such as heartbeat and changes between systolic and diastolic blood pressure. As shown in FIG. 2, a band 200 may be provided to wrap around an appendage, such as the wrist A of a user. A blood pressure sensor 230 that includes an FBG may be placed within the band, and configured to detect slight changes in the user's skin, particularly near an artery such as the radial artery B. By measuring the surface deformation in the skin, the device 200 can detect and track the periodic movement caused by a user's pulse (for example the radial pulse) that results from pressure waves due to changing arterial blood pressure as the beating heart pumps oxygenated blood through the body. While counting the number of signal pulses in a prescribed time can be used to detect the pulse rate.

A more comprehensive description of the cardiopulmonary function is derived from the hemodynamic monitoring, wherein the circulatory function is assessed repeatedly over time. Perturbations in the circulatory function is expected under physiologic stress, surgery, or acute illness. Hemodynamic monitoring is often performed in a clinical environment using invasive methods to accurately measure the blood pressure pulse in high fidelity. The measured data is analyzed for deriving parameters such as the stroke volume (SV) and cardiac output (CO=SV×HR) for a comprehensive assessment of cardiovascular insufficiency and tissue oxygenation. Hemodynamic monitoring is critically important for heart failure, hypovolemia, and septic shock due to infections. Recently there have been developments of non-invasive hemodynamic monitoring, but such methods are still used in the clinical setting. Example embodiments can provide for performing ambulatory and non-invasive hemodynamic monitoring, thereby allowing for a more accurate tracking of the cardiopulmonary function at the population level that is not possible via conventional devices.

Additionally, the device can measure the user's blood pressure by using a calibration function that correlates the change in Bragg wavelength (and in turn the induced strain) caused by the deformation of the FBG by the pulses into to a pressured required to induce that change Another sensor serves as a baseline sensor 270 that includes an optical fiber with an embedded FBG located away from the artery B can perform a real time baseline measurement. Based on a calibration function comparing pressure against strain or wavelength, along with the strain data from these two sets of sensors, one can detect both the Systolic and the Diastolic blood pressure.

Pulse Transit Times (PTT), the time interval between the peak of the R wave in ECG and Blood Pressure Pulses or Heart Rate can be used to compute the systolic and diastolic blood pressure. As a result, the blood pressure can be obtained using pulse time difference and correlation methods between the pressure pulses measured by the blood pressure monitor and the ECG pulses and/or the heart rate monitor and/or pulsatile data measured by the pulse oximetry device.

Before one can use the embedded FBG as a strain gauge, the FBG's response function and linearity should be characterized as a function of load. To characterize the FBG's response function and linearity, an electrical strain gauge may be used to calibrate the FBG such that the applied tensile loading approximates readings of the displacement of the users skin due to the flow of blood. Once calibrated, the response of an FBG may be reliably used as an embedded strain gauge for detecting object surface deformation.

For the FBG to perform as a reliable strain gauge, the change in the reflection wavelength of the FBG as it gets stretched under tensile load must linearly track the electrical strain gauge data. It has been shown that the Bragg wavelength shift for an embedded FBG under tensile loading is linearly correlated with the induced strain as measured using an electrical strain gauge within the elastic limit. It is also known that in the low strain regime which is the case in the current application, the stress which is defined as the tensile loading divided by the cross-sectional area (in unit of pressure) is linearly correlated with the induced strain with the constant of proportionality being the modulus of elasticity. This is the classical definition of Hooke's law. Based on the above two linear relationships, one can deduce that the stress is linearly correlated with the Bragg wavelength is linearly correlated with stress. It is this proportionality that one exploits to deduce the blood pressure from the Bragg wavelength shift in an embedded FBG. Within reasonable limits on the elasticity of the gauge, it may also be used for detecting the degree to which the object surface has been displaced for purposes of detecting a blood pressure reading.

Referring back to device 200, the FBG sensor is embedded longitudinally along the band 200, typically running in a direction perpendicular to the blood flow of a major artery or vein B. The band 200 may have an input 225 for a laser or light source that is transmitted through the FBG 230. The FBG 230 is connected to a light sensor 220 that receives pulsed light waves from the light source 225. The light sensor is connected to a processor 210 configured to analyze the data concerning the light transmissions through the FBG 230. The processor 210 identify shifts in the refractive index of the FBG 230 and calculate the user's blood pressure based on those readings. In addition to reading blood pressure, the FBG sensors can also be used to measure pulse rates by detecting the periodic changes in surface deformation caused by the pumping of blood through the user's circulatory system.

In the embodiment shown in device 200, the blood pressure calculation and/or pulse rates can then be sent by transmitter 240 to an application on an external device (not shown) such as a mobile phone or handheld reader. The band may be designed to communicate wirelessly over Bluetooth, cellular data, local WiFi, or some other wireless transmission. The embodiment shown in device 200 also provides a localized display 250, allowing for a real-time reading of the user's blood pressure and other readings without the use of an external device reader. The circuitry in the band may be include other known elements known to those skilled in the art, such as wireless communications circuitry, energy storage, and other processors not shown.

Thus, the band 200 may provide blood pressure and pulse rates using one or more embedded FBG sensors can be used as a standalone blood pressure monitor that is free of a physically moving part such as a pump used in current versions of blood pressure monitors making them robust against environmental conditions as well as more cost effective to manufacture. Having a wearable blood pressure monitor, and health monitor in general, that is free of any wired connections, and cumbersome devices (such as pumps and inflatable cuffs), that can have a user display and/or transmit the health data remotely for viewing or monitoring may be used in both a hospital or health care setting.

While such a device may be particularly helpful in those situations where a patient needs to be monitored, personal health monitoring devices have become increasingly popular, and allow individuals with non-critical needs to track their wellness. Tracking vitals such as blood pressure, cardiac output, ECG, blood oxygen, and blood glucose levels can lead to early detection of many conditions, such as sleep apnea through blood oxygen monitoring; acute heart conditions such as heart failure, hypovolemia; and presence of chronic conditions such as Patent Foramen Ovale ("PFO") and Atrial Septal Aneurysm ("ASA") through combined blood pressure and blood oxygen monitoring. Additionally, real time measurement of the Blood Pressure pulse wave-form in full detail will open up new ways to assess pulmo-nary function as well as early indications of hypovolemic shock through decreased cardiac output; and septic, or neurogenic shock through the measurement of the dicrotic notch location. With the advent of big data analytics and artificial intelligence, comprehensive vitals data from indi-viduals and population can be mined to detect and predict conditions that are not possible today. A health monitor consistent with principles of the present invention can go far beyond the wellness and activity monitors and become a potent tool in preventive healthcare.

The wearable band 200 should be constructed from a thin elastic, or otherwise pliable material, such as a stretchable fabric, that enables some movement of the material over a user's skin, as the band is configured to fit around a body part of the user. The band may be made of constructed to hold the FBG 230 against the body part to which the surface deformation is to be detected. The band material should have sufficient elasticity such that the rigidity of the band material does not interfere with the flexion of the optical fiber and FBG embedded within it.

Other embodiments consistent with principles of the invention could use multiple FBGs embedded in the band to acquire a number of different readings that could be recon-ciled with one another to provide a more accurate calcula-tion of the blood pressure. In other embodiments multiple FBGs separated by fixed distances could also be embedded in the band along the length of a single optical fiber with an angled cleave termination.

Figures 3A, 3B:
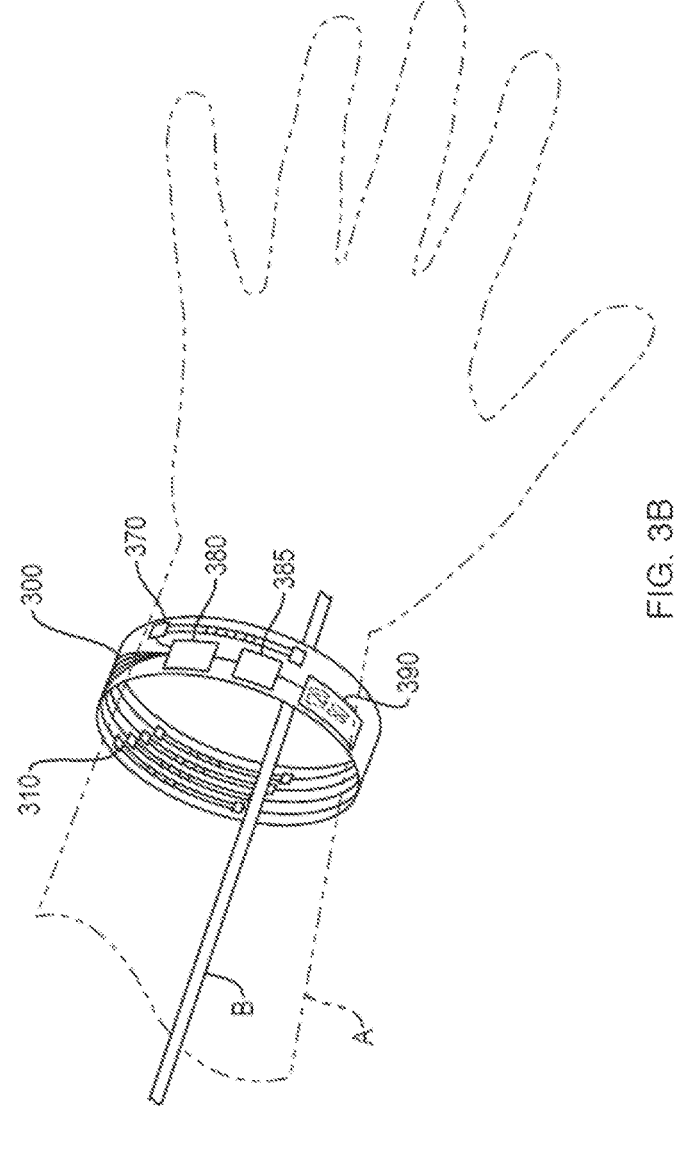
FIG. 3A is a representative set of fibers having FBGs configured in parallel arrangement.
FIG. 3B is an exemplary wearable health monitoring device consistent with principles of the invention implementing the set of fibers shown in FIG. 3A.

FIGS. 3A and 3B illustrate another embodiment consis-tent with principle of the invention. FIG. 3A shows a sensor strip 310 having a set of optical fibers 320, 330, 340 and 350 with embedded FBGs 325a-n, 335a-n, 345a-n, and 355a-n, that are slightly displaced from each other. In FIG. 3B, the wearable band 300 includes a blood pressure sensor 310 that includes multiple optical fibers as shown in FIG. 3A. The optical fibers of the sensor strip 310 span a region that is directly over the radial artery B, and as an example, may measure the pulse shape. Another embedded optical fiber 370 with an embedded FBG is located away from the artery to perform a real time baseline measurement. Each of the optical fibers 320, 330, 340, 350 and 370 use both light source and light sensor (not shown) in order to provide pulsed light waves data to a processor 380. The band 300 shown in FIG. 3B also has a transmitter 385 that allows the band 300 to send data to an application on an external device (not shown) such as a mobile phone or handheld reader. Additionally, the band 300 also provides a localized display 390.

Similarly, while the optical fibers and FBGs shown in FIG. 2 and FIG. 3B are embedded longitudinally along the band 200, in alternate embodiments, data may be acquired by one or more FBGs embedded perpendicular to the length of the band, with the processor analyzing the deformations accordingly.

Figure 3C:
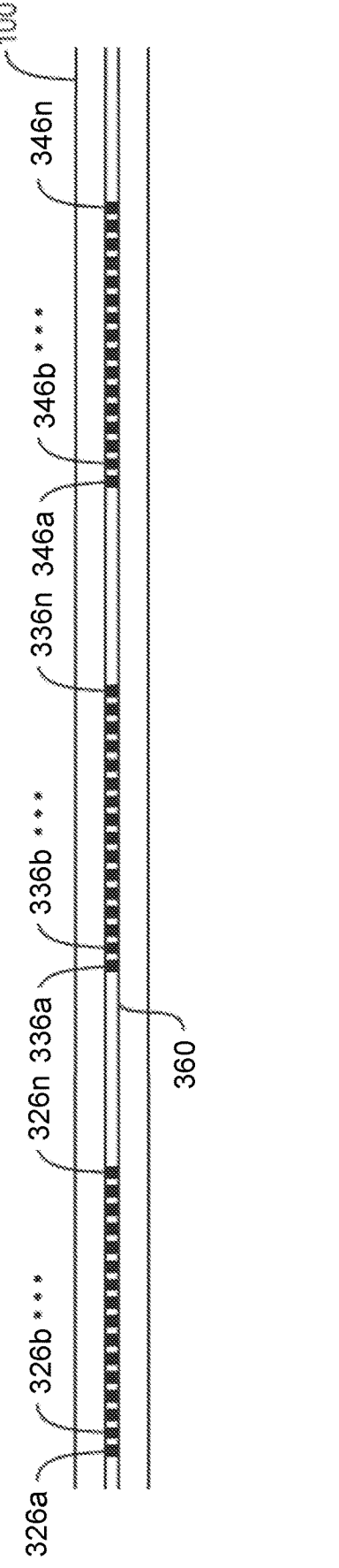
FIG. 3C is a representative set of fibers having FBGs configured in a serial arrangement.

FIG. 3C shows a sensor strip 312 having an optical fiber 360 with a plurality of embedded FBGs 326a-n, 336a-n, and 346a-n, which are arranged serially along the optical fiber 360. The sensor strip 312 may be implemented in the wearable band 300 as an alternative to the sensor strip 310 described above. In such an implementation, the sensor strip 312 may span multiple revolutions along the band 300, and/or may arrange multiple FBGs serially within a single revolution along the band 300.

In addition, in other embodiments consistent with prin-ciples of the invention, a blood pressure monitor described above may also be combined with other miniaturized physi-ological monitors (ECG, blood oxygen saturation, body temperature, and blood glucose measurements using known contact temperature sensors and optical methods) to make a comprehensive wearable health monitor.

Figure 4:
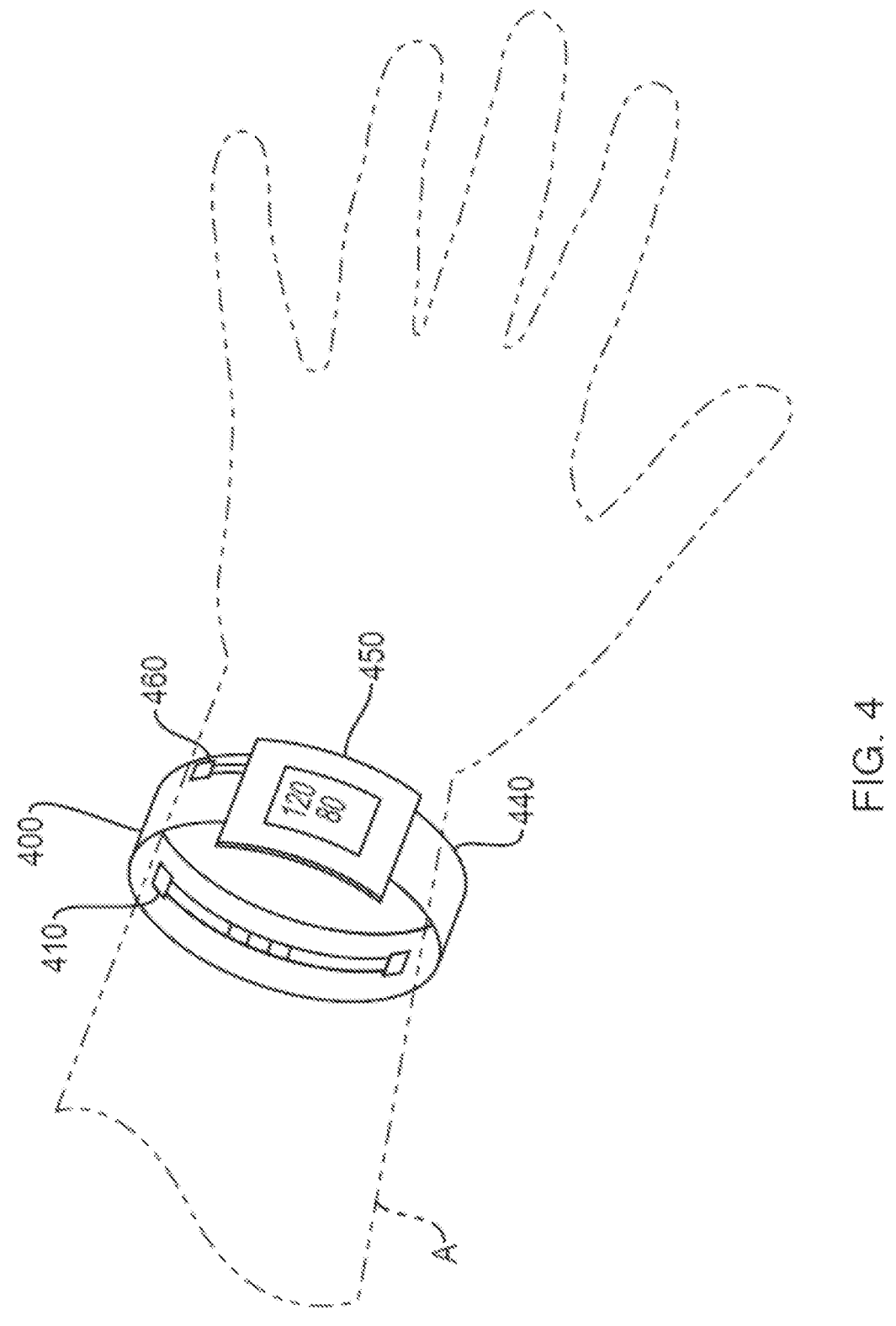
FIG. 4 is an exemplary wearable health monitoring device consistent with principles of the invention.

FIG. 4 illustrates yet another embodiment consistent with principles of the present invention. In FIG. 4, the wearable blood pressure monitoring system 400 is comprised of a blood pressure processing unit 450 and a detachable band 440. The detachable band 440 includes a least one blood pressure sensing optical fiber 410 with an FBG, and a baseline optical fiber 460 with an FBG. The blood pressure processing unit 450 contains internal electronics (not shown) that enable the pulsing of a laser or light through the optical fibers 410 and 460 of the band 440, the sensing of the refractive indices through the fibers, and the processing of the indices to determine the blood pressure of the wearer A. The band 440 is removably connected to the blood pressure processing unit 450, such that upon connection, unit 450 can pulse a laser or light through the band 440. As a wearable device, the band 440 may become dirty or damaged. How-ever, as a removable component of the device, the band 440 may be easily replaced with minimal cost.

Figure 5:
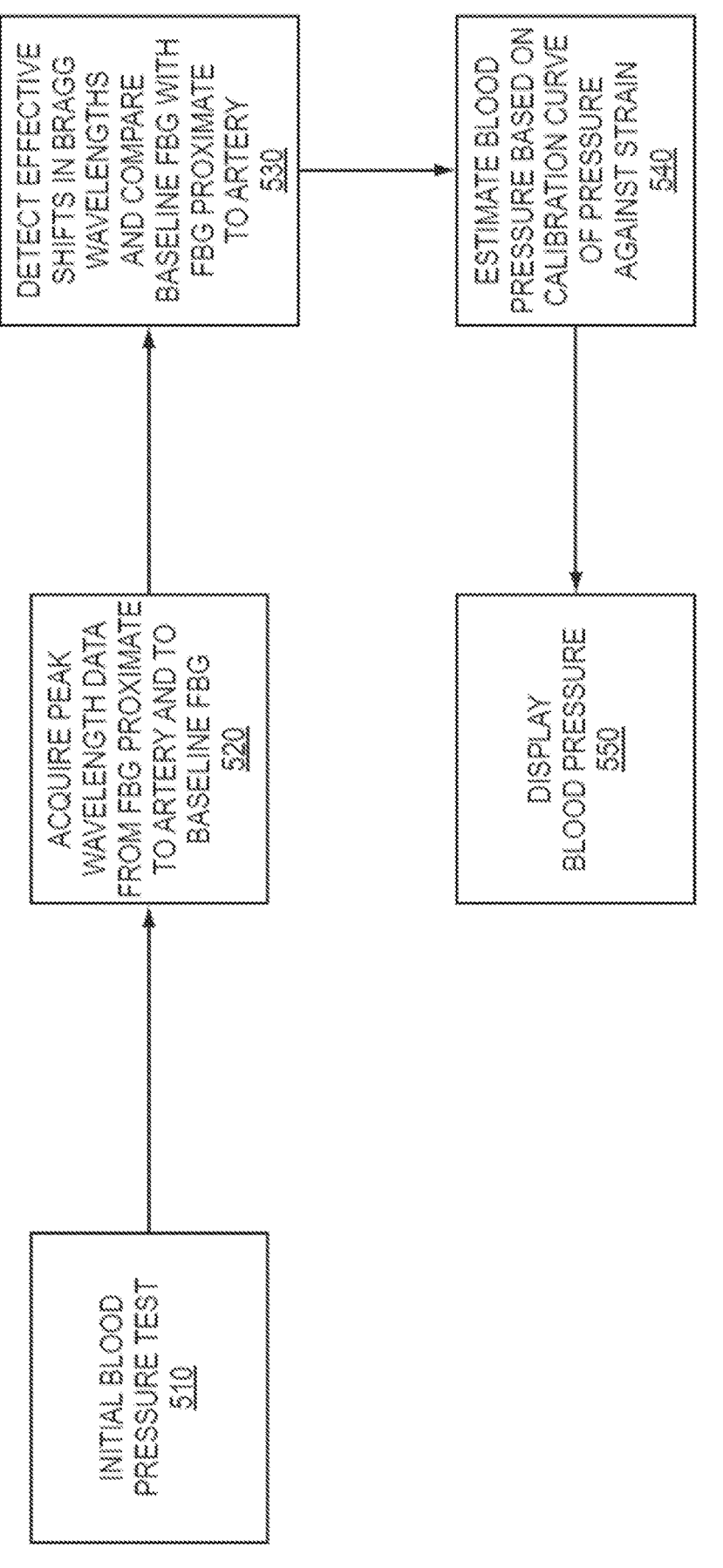
FIG. 5 is a flowchart illustrating the method of estimating blood pressure using FBG measurement consistent with principles of the invention.

FIG. 5 is a flowchart illustrating a method 500 of detect-ing blood pressure using an wearable item embedded with a fiber Bragg grating FBG. The blood pressure detection may be initiated by a user, or blood pressure may be periodically detected and monitored. Once initiated, peak wavelength data is acquired at step 510 from at least one FBG disposed along the wearable item. Data is continually acquired and the user's skin is monitored for effective shifts of the Bragg wavelengths of the FBGs caused by surface deformation at step 520. As a shift is detected 530, the data is processed to calculate an estimated systolic and diastolic blood pressure 540. The estimated systolic and diastolic blood pressure are then displayed at step 550.

Figure 6:
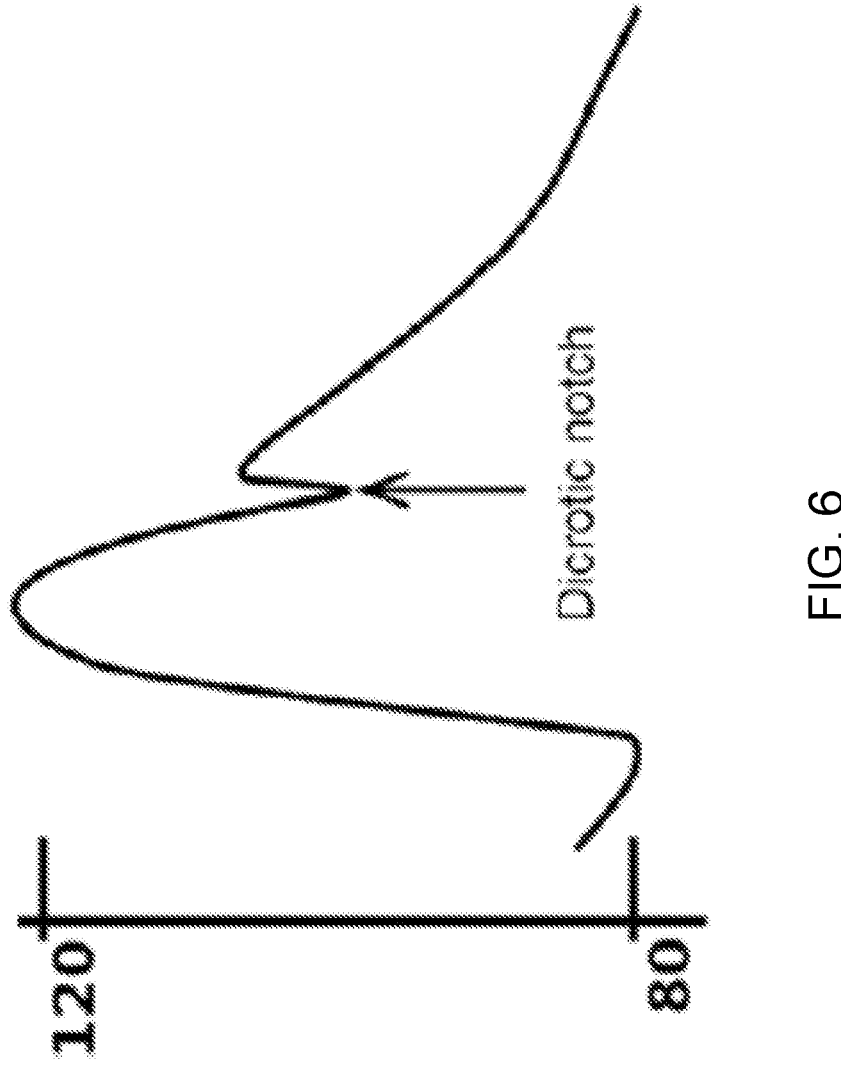
FIG. 6 is a plot of a blood pressure waveform that may be measured in example embodiments.

FIG. 6 is a plot of a blood pressure waveform that may be measured in example embodiments. The arterial blood pres-sure waveform is produced through the dynamic interaction between the cardiac stroke and the vascular tree. The pri-mary features of the waveform are defined by the systole, closure of the aortic valve, and diastole. The peak of the waveform that occurs just after the QRS complex of the ECG and reflects the systolic pressure with the area under this peak defined as the stroke volume, the aortic valve closure is reflected by the dicrotic notch, which is followed by a down stroke that ends in diastole. Many anatomical and physiological factors affect the waveform for a given indi-vidual.

The teachings of all patents, published applications and references cited herein are incorporated by reference in their entirety.

While example embodiments have been particularly shown and described, it will be understood by those skilled in the art that various changes in form and details may be made therein without departing from the scope encompassed by the appended claims.

It should be understood that the example embodiments described above may be implemented in many different ways. In some instances, the various methods and machines described herein may each be implemented by a physical, virtual or hybrid general purpose computer having a central processor, memory, disk or other mass storage, communication interface(s), input/output (I/O) device(s), and other peripherals. The general purpose computer is transformed into the machines that execute the methods described above, for example, by loading software instructions into a data processor, and then causing execution of the instructions to carry out the functions described, herein.

As is known in the art, such a computer may contain a system bus, where a bus is a set of hardware lines used for data transfer among the components of a computer or processing system. The bus or busses are essentially shared conduit(s) that connect different elements of the computer system, e.g., processor, disk storage, memory, input/output ports, network ports, etcetera, which enables the transfer of information between the elements. One or more central processor units are attached to the system bus and provide for the execution of computer instructions. Also attached to system bus are typically I/O device interfaces for connecting various input and output devices, e.g., keyboard, mouse, displays, printers, speakers, etcetera, to the computer. Network interface(s) allow the computer to connect to various other devices attached to a network. Memory provides volatile storage for computer software instructions and data used to implement an embodiment. Disk or other mass storage provides non-volatile storage for computer software instructions and data used to implement, for example, the various procedures described herein.

Embodiments may therefore typically be implemented in hardware, firmware, software, or any combination thereof.

In certain embodiments, the procedures, devices, and processes described herein constitute a computer program product, including a non-transitory computer-readable medium, e.g., a removable storage medium such as one or more DVD-ROM's, CD-ROM's, diskettes, tapes, etcetera, that provides at least a portion of the software instructions for the system. Such a computer program product can be installed by any suitable software installation procedure, as is well known in the art. In another embodiment, at least a portion of the software instructions may also be downloaded over a cable, communication and/or wireless connection.

Further, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etcetera.

It also should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and, thus, the data processors described herein are intended for purposes of illustration only and not as a limitation of the embodiments.

While this invention has been particularly shown and described with references to example embodiments thereof, it will be understood by those skilled in the art that various changes in form and details may be made therein without departing from the scope of the invention encompassed by the appended claims.

What is claimed is:

1. A health monitoring device, comprising:
   a blood pressure sensor including a first fiber Bragg grating (FBG) configured to be placed in contact with a person's skin approximate to an artery or vein and having a first Bragg wavelength;
   a baseline sensor including a second fiber Bragg grating (FBG) configured to be placed in contact with a person's skin away from the artery or vein and having a second Bragg wavelength and providing a measure of a baseline signal;
   a light emitter configured to pulse light waves through the FBGs;
   light sensors configured to receive pulsed light waves;
   a processor including:
      a data acquisition module configured to receive from the light sensor peak wavelengths reflected by the FBGs;
      a comparator configured to determine effective shifts of the first Bragg wavelength and effective shifts of the second Bragg wavelength over time; and
      a blood pressure estimator configured to estimate systolic and diastolic blood pressure based on 1) the effective shifts of the first Bragg wavelength corrected for drifts in the baseline signal based on the effective shifts of the second Bragg wavelength, and 2) an output of a physiological attribute monitor; and
   a display for providing the estimated systolic and diastolic blood pressure.

2. The device of claim 1, wherein the blood pressure estimator is configured to estimate the systolic and diastolic blood pressure based on pulse transit times (PTT) between blood pressure pulses from the blood pressure sensor and the output, the output being one of an electrocardiogram (ECG) and a heart rate monitor.

3. The device of claim 1, wherein the processor is further configured to determine a pulse pressure waveform based on the effective shifts of the first Bragg wavelength corrected for drifts in the baseline signal based on the effective shifts of the second Bragg wavelengths.

4. The device of claim 3, wherein the processor is further configured to analyze pulse pressure waveform features including at least one of a stroke volume and a dicrotic notch.

5. The device of claim 3, further comprising a processor configured to analyze the pulse pressure waveform to determine a cardiovascular parameter including at least one of stroke volume and cardiac output.

6. The device of claim 3, further comprising a processor configured to perform a pattern recognition analysis of the pulse pressure waveform to estimate a likelihood of a disease exhibited by the person.

7. The device of claim 1, implemented in a wearable band at the person's arm or wrist, the first and second FBGs being embedded within a strap of the wearable band.

8. The device of claim 7, wherein the physiological attribute monitor is enclosed within the device the physiological attribute monitor including at least one of an ECG, a heartrate monitor, an oxygen saturation (SPO2) monitor, a blood glucose monitor, and a skin temperature monitor.

9. The device of claim 1, wherein the blood pressure estimator is configured to estimate the systolic and diastolic blood pressure based on a calibration function is derived from a timing correlation between the blood pressure sensor and an output of the physiological attribute monitor, the output being at least one of an ECG, heart rate, blood oxygen saturation.

10. The device of claim 1, wherein the processor further includes a heart rate monitor configured to detect periodic changes in surface deformation associated with a heartbeat.

11. The device of claim 1, wherein the physiological attribute monitor measures one of an ECG, blood oxygen saturation, body temperature, and blood glucose.

12. The device of claim 1, wherein the display is located on a remote device, and further including a transmitter configured to transmit estimated systolic and diastolic blood pressure to the display.

13. The device of claim 1, wherein the blood pressure sensor further includes a plurality of FBGs configured to be placed in contact with a person's skin close approximate to an artery or vein and having Bragg wavelengths, wherein each FBG is displaced from one another by a predetermined amount, and wherein the processor is configured to reconcile acquired data from the plurality of FBGs to optimize a measurement in effective shifts in Bragg wavelength of the blood pressure sensor.

14. A method of monitoring health, comprising:

pulsing light waves through a first and second fiber Bragg gratings (FBGs) at 1) a blood pressure sensor including a first fiber Bragg grating (FBG) configured to be placed in contact with a person's skin approximate to an artery or vein and having a first Bragg wavelength, and 2) a baseline sensor including a second fiber Bragg grating (FBG) configured to be placed in contact with a person's skin away from the artery or vein and having a second Bragg wavelength and providing a measure of a baseline signal;

obtaining, from a light sensor configured to receive pulsed light waves, peak wavelengths reflected by the first and second FBGs;

determining effective shifts of the first Bragg wavelength and effective shifts of the second Bragg wavelength over time;

estimating systolic and diastolic blood pressure based on
1) the effective shifts of the first Bragg wavelength corrected for drifts in the baseline signal based on the effective shifts of the second Bragg wavelength, and 2) an output of a physiological attribute monitor; and displaying the estimated systolic and diastolic blood pressure.

15. The method of claim 14, wherein estimating the systolic and diastolic blood pressure is based on pulse transit times (PTT) between blood pressure pulses from the blood pressure sensor and the output, the output being one of an electrocardiogram (ECG) and a heart rate monitor.

16. The method of claim 14, further comprising determining a pulse pressure waveform based on the effective shifts of the first Bragg wavelength corrected for drifts in the baseline signal based on the effective shifts of the second Bragg wavelengths.

17. The method of claim 16, further comprising analyzing pulse pressure waveform features including at least one of a stroke volume and a dicrotic notch.

18. The method of claim 16, further comprising analyzing the pulse pressure waveform to determine a cardiovascular parameter including at least one of stroke volume and cardiac output.

19. The method of claim 16, further comprising performing a pattern recognition analysis of the pulse pressure waveform to estimate a likelihood of a disease exhibited by the person.

20. The method of claim 16, wherein estimating the systolic and diastolic blood pressure is based on a calibration function derived from a timing correlation between the blood pressure sensor and an output of the physiological attribute monitor, the output being at least one of an ECG, heart rate, blood oxygen saturation.

* * * * *